US009627837B1

(12) United States Patent
Krupica

(10) Patent No.: US 9,627,837 B1
(45) Date of Patent: Apr. 18, 2017

(54) MEDICAL LASER SYSTEM

(71) Applicant: Lymol Medical, Inc., Woburn, MA (US)

(72) Inventor: Libor Krupica, Nashua, NH (US)

(73) Assignee: Lymol Medical, Inc., Woburn, MA (US)

( * ) Notice: Subject to any disclaimer, the term of this patent is extended or adjusted under 35 U.S.C. 154(b) by 0 days.

(21) Appl. No.: 15/088,940

(22) Filed: Apr. 1, 2016

Related U.S. Application Data

(60) Provisional application No. 62/312,272, filed on Mar. 23, 2016.

(51) Int. Cl.
*H01S 3/04* (2006.01)
*H01S 3/16* (2006.01)
*H01S 3/042* (2006.01)
*A61B 18/20* (2006.01)
*A61B 18/00* (2006.01)

(52) U.S. Cl.
CPC ............ *H01S 3/0407* (2013.01); *A61B 18/20* (2013.01); *H01S 3/042* (2013.01); *H01S 3/1638* (2013.01); *A61B 2018/00023* (2013.01)

(58) Field of Classification Search
CPC ...... H01S 3/0407; H01S 3/0405; H01S 3/042; H01S 3/1638; A61B 18/20; A61B 2018/00023; A61B 2018/00011
See application file for complete search history.

(56) References Cited

U.S. PATENT DOCUMENTS

| 5,312,396 A | 5/1994 | Feld et al. |
| 5,802,087 A * | 9/1998 | Takaichi ............ H01S 3/042 372/35 |
| 2002/0002367 A1* | 1/2002 | Tankovich ............ A61B 18/22 606/3 |
| 2006/0060333 A1* | 3/2006 | Chordia ............. F28D 15/0266 165/104.33 |

(Continued)

FOREIGN PATENT DOCUMENTS

WO 2013033145 A1 3/2013

OTHER PUBLICATIONS

Barco,Inc., "Installation Manual—Cooling Liquid Refurbishment," R59770032, Barco nv Events, 22 pages, 2006.

(Continued)

Primary Examiner — Armando Rodriguez
(74) Attorney, Agent, or Firm — Foley Hoag LLP; Rajesh Vallabh

(57) ABSTRACT

A medical laser system includes a crystal-based laser, a power supply for powering the crystal-based laser, a controller operably connected to the crystal-based laser and the power supply, and a liquid cooling system. The liquid cooling system includes a conduit circuit through which a cooling liquid can circulate. The conduit circuit is thermally coupled to the crystal-based laser such that the cooling liquid in the conduit circuit absorbs heat from the crystal-based laser. One or more heat sinks are coupled to the conduit circuit and to the power supply such that the cooling liquid in the conduit circuit absorbs heat from the power supply. A pump is provided for driving the cooling liquid through the conduit circuit. A heat exchanger cools the cooling liquid in the conduit circuit.

23 Claims, 5 Drawing Sheets

(56) References Cited

U.S. PATENT DOCUMENTS

2006/0084953 A1    4/2006  Tankovich

OTHER PUBLICATIONS

Bryan Corporation, "Lokki Lis Laser," Brochure, 2 pages, 1995.
Huang et al., "1.3414 mm Nd: YAP pulse laser in Q-switched mode," Optics Communications, vol. 260, Issue 1, 1 Apr. 2006, pp. 248-260. (Abstract).
Lee et al., "Initial Report of Neodymium: Yttrium-Aluminum-Perovskite (Nd: YAP) Laser Use During Bronchoscope," Journal of Bronchology & Interventional Pulmonology, Jul. 2011, vol. 18, Issue 3, pp. 229-232.

* cited by examiner

MEDICAL LASER SYSTEM

This application claims priority from U.S. Provisional Patent Application No. 62/312,272 filed on Mar. 23, 2016 entitled MEDICAL LASER SYSTEM, which is hereby incorporated by reference.

BACKGROUND

Surgical lasers are a well-known alternative to scalpels, curettes, and other mechanical tools used to surgically remove tissue. Directing intense near infrared (NIR) laser light onto tissue can cause the tissue to vaporize, burn, be ablated, or otherwise be cut. Less intense NIR laser light can be used to cause coagulation or cauterization.

Laser surgical instruments are often bulky and difficult to move from one operating venue to another. A need exists for an improved surgical laser, for example, a surgical laser with decreased size and/or better reliability.

SUMMARY

A medical laser system in accordance with one or more embodiments includes a crystal-based laser, a power supply for powering the crystal-based laser, a controller operably connected to the crystal-based laser and the power supply, and a liquid cooling system. The liquid cooling system includes a conduit circuit through which a cooling liquid can circulate. The conduit circuit is thermally coupled to the crystal-based laser such that the cooling liquid in the conduit circuit absorbs heat from the crystal-based laser. One or more heat sinks are coupled to the conduit circuit and to the power supply such that the cooling liquid in the conduit circuit absorbs heat from the power supply. A pump is provided for driving the cooling liquid through the conduit circuit. A heat exchanger cools the cooling liquid in the conduit circuit.

A medical laser system in accordance with one or more further embodiments includes a crystal-based laser, a power supply for powering the crystal-based laser, a controller operably connected to the crystal-based laser and the power supply, and a memory operably connected to the controller. The controller is programmed to: (a) activate the crystal-based laser to cause a laser light emission by controlling power supplied by the power supply to the laser responsive to a user activation input; and (b) record data in the memory identifying a power level, number of pulses, and duration of the laser light emission.

A medical laser system in accordance with one or more further embodiments includes a crystal-based laser, an electrosurgery or electrocautery device, a power supply for powering the crystal-based laser and the electrosurgery or electrocautery device, and a controller operably connected to the crystal-based laser, the electrosurgery or electrocautery device, and the power supply. The controller is programmed to: (a) activate the crystal-based laser by controlling power supplied by the power supply to the laser responsive to a laser activation input by a user; and (b) activate the electrosurgery or electrocautery device by controlling power supplied by the power supply to the electrosurgery or electrocautery device responsive to an electrosurgery or electrocautery device activation input by the user.

A medical laser system in accordance with one or more further embodiments includes a crystal-based laser configured, when activated, to emit laser light having wavelength in the range of 1000 to 2000 nanometers. The system also includes a pointer laser configured, when activated, to emit visible green or blue laser light having a wavelength in the range of 400 to 620 nanometers. The pointer laser and the crystal-based laser are configured to be focused on a common target position. The system also includes a power supply for powering the crystal-based laser and the pointer laser and a controller operably connected to the power supply, the crystal-based laser, and the pointer laser. The controller is programmed to: (a) activate the crystal-based laser by controlling power supplied by the power supply to the laser responsive to a laser activation input from a user; and (b) activate the pointer laser by controlling power supplied by the power supply to the pointer laser responsive to a pointer laser activation input from the user.

A method of using a surgical laser system in accordance with one or more further embodiments includes the steps of: (a) positioning an emission port of the laser system at a predetermined cutting distance from a tissue to be cut; (b) cutting the tissue to be cut by activating the laser system while the emission port is at the predetermined cutting distance from the tissue to be cut; (c) positioning the emission port at a predetermined coagulation distance from a tissue to be coagulated, the coagulation distance being greater than the cutting distance; and (d) coagulating the tissue to be coagulated by activating the system while the emission port is at the predetermined coagulation distance from the tissue to be coagulated.

DETAILED DESCRIPTION

Figure 1:
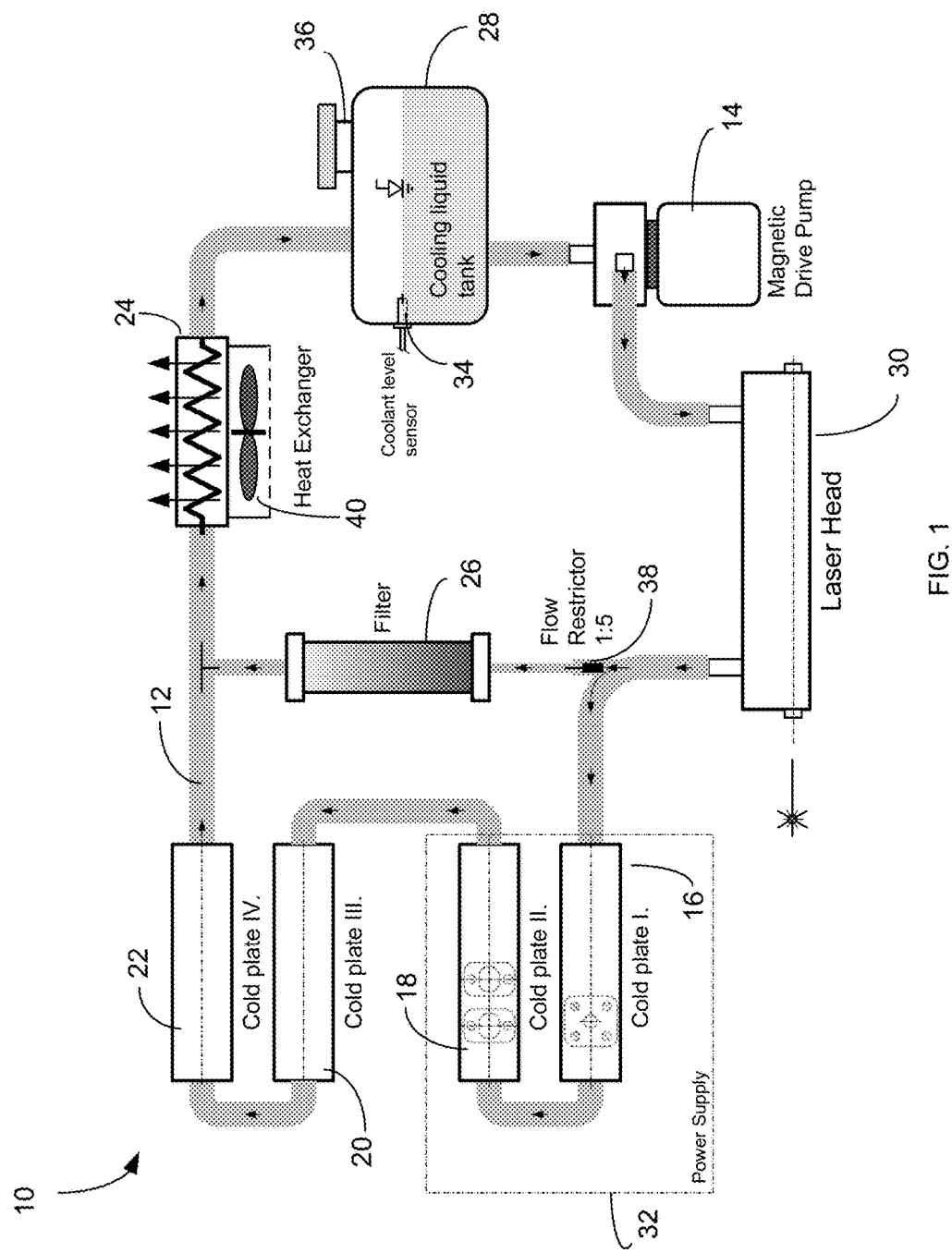
FIG. 1 schematically illustrates an exemplary cooling system for a medical laser in accordance with one or more embodiments.

FIG. 1 schematically illustrates an exemplary liquid cooling circuit 10 in a medical laser system in accordance with one or more embodiments. The liquid cooling circuit comprises a closed conduit circuit 12 through which cooling liquid flows, a pump 14, one or more cooling plates 16, 18, 20, 22, a heat exchanger 24, a filter 26, and a liquid replenishment tank 28. The cooling liquid inside the circuit absorbs heat from a laser head 30 and the one or more cooling plates. Heated liquid is transported to the heat exchanger, which cools the liquid.

The cooling liquid can comprise a variety of heat transfer fluids including, e.g., water including deionized water and distilled water.

The pump 14 can comprise a variety of pumps including, e.g., a magnetic drive pump. In the exemplary embodiment of FIG. 1, the pump drives the liquid through the circuit in a counterclockwise direction as indicated by the flow arrows.

The cooling circuit is coupled to the laser head such that cooling liquid can flow through the laser head housing in thermal contact with the laser components therein.

Figure 2:
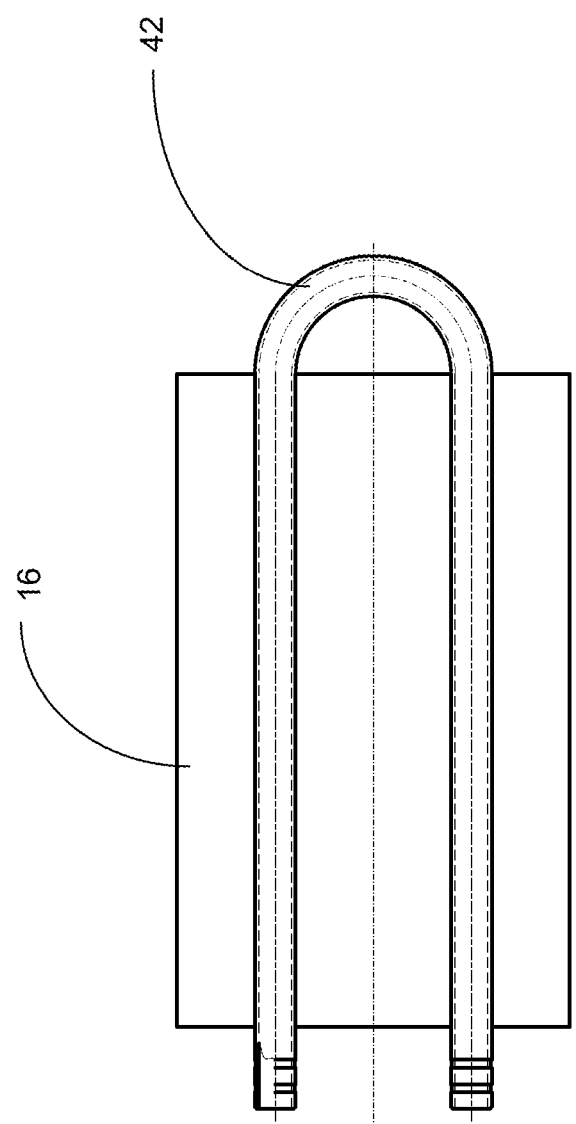
FIG. 2 is a cross-section view of an exemplary liquid cooled heat sink in the cooling system of FIG. 1 in accordance with one or more embodiments.

The cooling fluid can also be in thermal contact with other components of the medical laser system. As shown in FIG. 1, the cooling liquid is thermally coupled with the thermally conductive cooling plates 16, 18, 20, 22. The cooling plates are in thermal contact with various other components of the laser system in need of temperature regulation including, e.g., a power supply 32, capacitors, and other electronics. Although the system is shown with four cooling plates, any number is possible. FIG. 2 is a cross-section view of an exemplary cooling plate 16 having a conduit 42 embedded therein carrying the cooling liquid.

Cooling liquid in the fluid circuit can be replenished, as needed, with additional liquid from a replenishment tank 28. The cooling liquid tank includes a coolant level sensor 34 and an inlet 36 for receiving additional liquid as needed.

The filter 26 removes any particles in the cooling liquid. The filter is connected to the liquid cooling circuit in parallel instead of in series since all the coolant fluid will not typically need to be filtered on every revolution through the circuit. A flow restrictor 38 controls the amount of the liquid flowing through the filter. By way of example, the flow restrictor can have a 1:5 flow ratio (with the smaller flow flowing to the filter).

The heat exchanger 24 may be actively cooled by a fan 40. The fan 40 blows ambient air across the heat exchanger 24, which is in thermal contact with the cooling liquid flowing through the fluid circuit. In the exemplary embodiment of FIG. 1, the cooling circuit includes no active cooling element other than the heat exchanger 24.

Including only a single fluid circuit with the attendant single pump and single heat exchanger significantly improves reliability and reduces the size and complexity of the entire system. The closed fluid circuit can be arranged as shown, with the various elements generally in series, or it could be arranged with one or more elements arranged in parallel, or a combination of the two.

Figure 3:
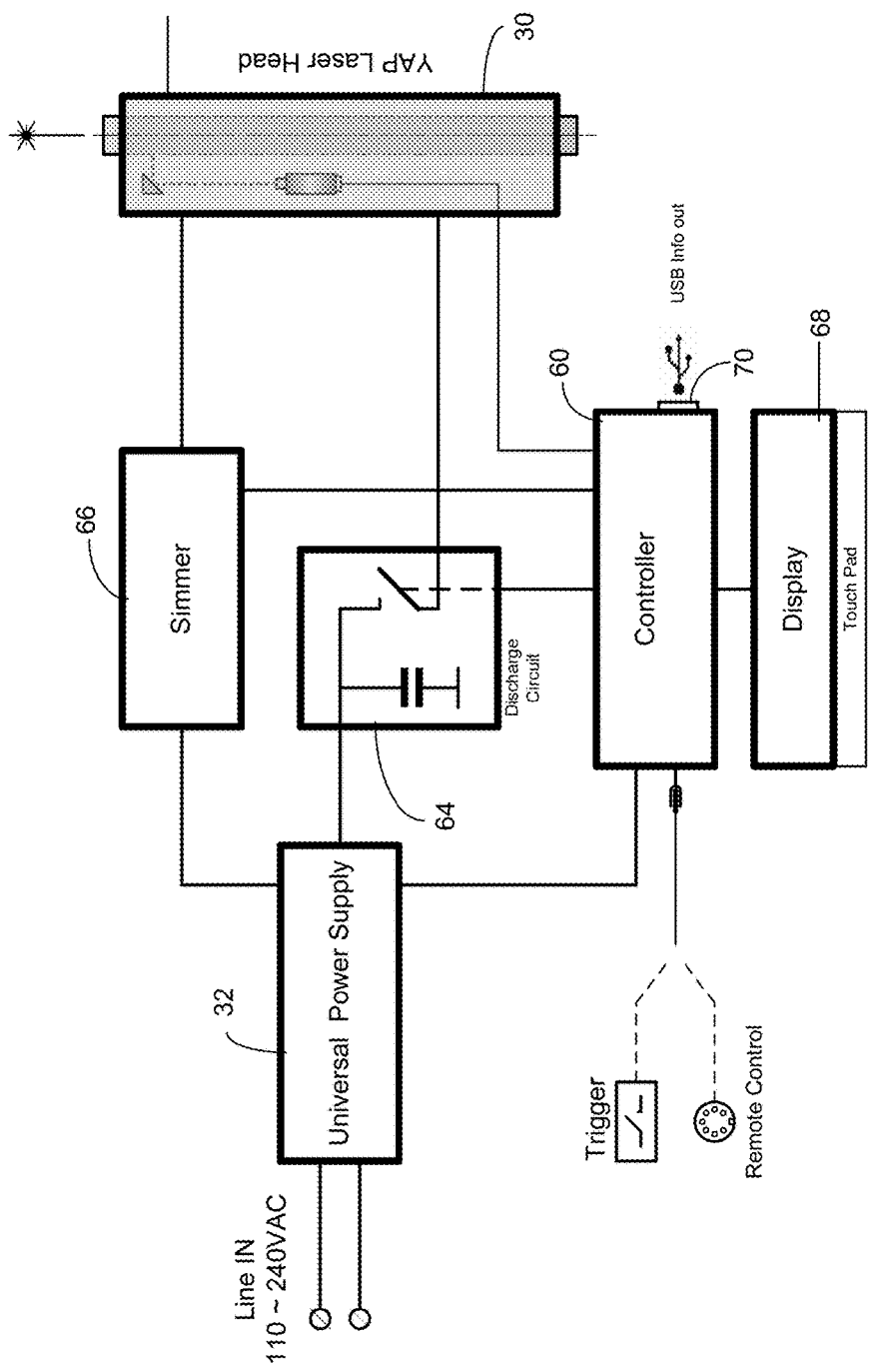
FIG. 3 schematically illustrates an exemplary control system for a medical laser in accordance with one or more embodiments.

FIG. 3 is a schematic block diagram of an exemplary control system for the laser system. The control system includes a controller 60 operably connected to the laser head 30, a power supply 32, a discharge circuit 64, a simmer module 66, and a display 68, which may have a touch interface. The controller may also be connected to control the operation of the coolant pump 14 and heat sink fan 40. The controller 60 can receive various inputs from (and provide outputs to) users through the touch interface, switches, or a remote control device to allow users to access different functions of the system. For example, the system can include inputs to allow the user to activate and deactivate the laser, and operate the laser in various different modes, including modes that vary the pulse length, pulse frequency, and instantaneous energy output.

The controller 60 is connected to a memory 70. As shown in FIG. 3, the memory 70 is physically adjacent to the controller, but can alternatively be connected to the controller without physical proximity, e.g., via a computer network such as the internet or a local area network. The memory can comprise a variety of memory devices including, e.g., a USB flash drive, a secure digital (SD) card, a micro SD card, a compact flash (CF) memory, hard disk, or floppy disk. If networked, the memory may be physically remote from the device, e.g., attached to a separate networked computer. Such a remote computer could be present in a central location in the same hospital as the surgical laser system, or could be even more physically remote, for example at a location of the system's manufacturer, or a vendor responsible for maintenance of the system. The memory could also be linked directly to a patients electronic medical records, or any other relevant record keeping database, e.g., an occupational hazard database. The memory can collect and record data relevant to a particular procedure or type of procedure, a particular patient, and/or the particular system to which the memory is attached or elements of that system. The memory can be used to record a wide variety of types of information, for example: the dosage of radiation emitted by the laser, duration of activation of the laser, the wavelength or wavelengths of light emitted by the laser, instantaneous power emitted by the laser, the time averaged power emitted by the laser, the time that a single element of the laser system (e.g., the pump, or the bulb) has been in use, the time that the entire system has been in use, the number of times the system has been used, the time since or time until a scheduled maintenance of the system or some element of the system. Each of these variables can be recorded for a single procedure, for a particular patient, or for all uses of the instrument. Because the controller digitally outputs all relevant data to the memory, no surgical staff need to manually time and measure the application of the surgical laser in a surgery. This function can be fully automated.

The system can be configured so that the surgical laser emits near-infrared (NIR) light generally in the range of 1000 nm to 1500 nm. In this wavelength range, especially at the long wavelength end of the range, the water present in tissue is highly absorptive, making cutting, ablating or vaporization of tissue effective. Also in this wavelength range, certain constituents of blood are highly absorptive and can be efficiently caused to clot. In particular, clotting of blood is most efficiently achieved by NIR light of about 1100 nm. A good compromise wavelength that is effective both to encourage clotting when applied at lower intensities, and also to destroy tissue if applied at higher intensities, is about 1341 nm.

The emission port of the laser can have a variety of different opening angles. One preferred opening angle is about 17 degrees. By using a single laser at about 1341 nm wavelength a surgeon can either cut or coagulate tissue: by holding the emission port close to the tissue to be destroyed, the surgeon can concentrate the emitted laser light into small area with high flux to cut; by holding the emission port farther from the tissue, the surgeon can spread the laser light over a larger area with lower flux in order to cause coagulation without cutting tissue. The single laser can perform both tasks simply by being between greater and smaller distances from the tissue.

Figure 4:
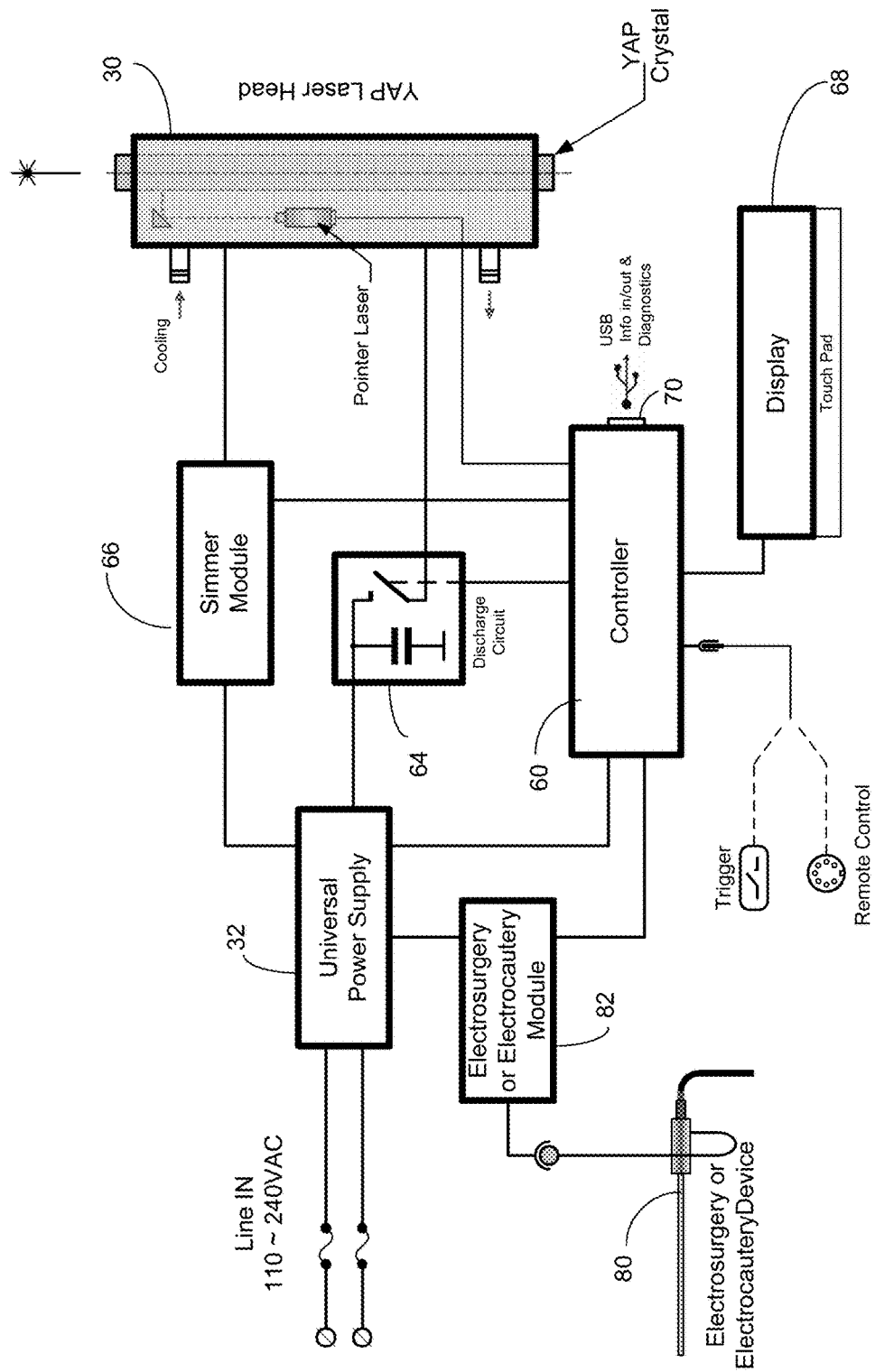
FIG. 4 schematically illustrates an exemplary control system for a laser and electrosurgery or electrocautery system in accordance with one or more embodiments.

The power supply 32 can be in some embodiments a programmable power supply, and can be made with more than one power output. While one power output is connected to the laser 30, another output could be connected to another electrical device. For example, the power supply 32 could include an outlet arranged to provide RF power, e.g., for an electrocautery or electrosurgery device 80 through an electrosurgery or electrocautery module 82 as shown in FIG. 4. The electrosurgery or electrocautery device 80 can thereby be conveniently powered by the power supply 32 on the surgical laser system and integrated in the laser system. In either case, the programmable power supply could be switched between a first mode in which power was supplied to the laser and a second mode in which power was supplied to the electrosurgery or electrocautery device 80 or another instrument. In one exemplary use an electrocautery element is operated to cause cutting of tissue or coagulation.

Figure 5:
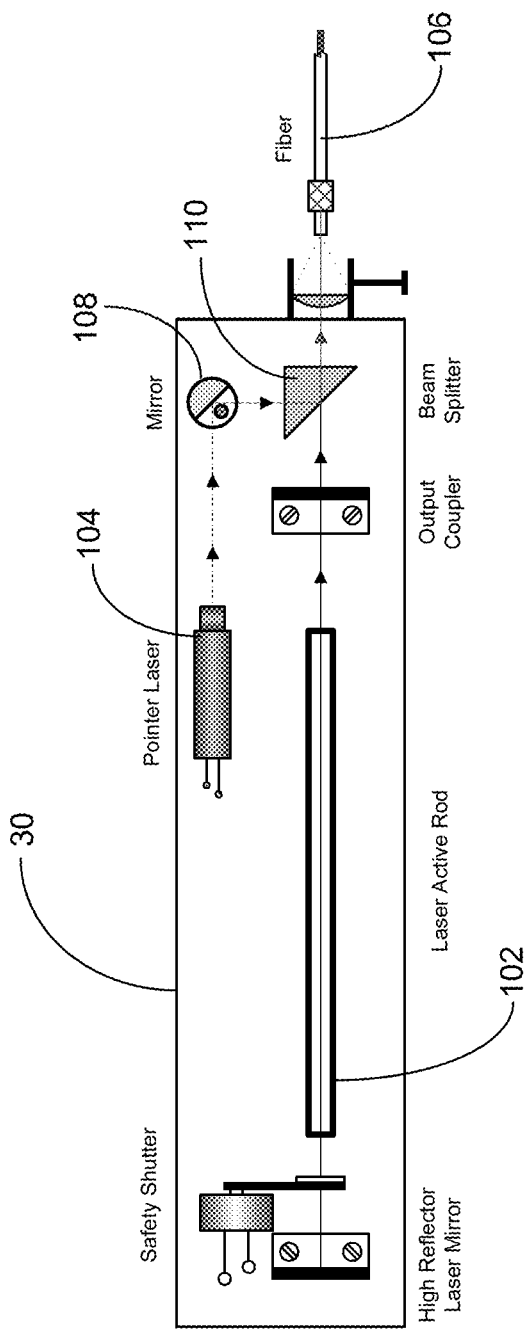
FIG. 5 schematically illustrates an exemplary laser head configuration of a medical laser in accordance with one or more embodiments.

FIG. 5 schematically illustrates an exemplary laser head configuration in accordance with one or more embodiments. The laser head 30 includes a non-coaxial arrangement of a laser active rod of a surgical laser 102 and a pointer laser 104. In the usual way, the surgical laser 102 directs light into a fiber optic cable 106. The laser light is emitted from the emission port at a distal end of the fiber optic cable. The pointer laser directs its visible light along a path that does not include the surgical laser, but instead is directed via optical elements (mirror 108 and beam splitter 110) onto the same path as the surgical laser light. In the exemplary configuration of FIG. 5, the beam from the pointer laser is formed generally parallel to, but non-coaxial with, the surgical laser beam, then turned 90 degrees by the mirror 108, then turned 90 degrees again by a beam splitter (combiner) 110. The combined surgical and pointer laser beams are then directed through the fiber optic 106 and emerge from the distal emission port. Visible laser pointer beams are important in the use of infrared surgical beams since the surgical beams are generally invisible. By setting the pointer laser off the axis of the surgical laser, the entire system can be made smaller and more portable. One particularly advantageous type of pointer laser is a green laser having a wavelength of around 500 nm to around 550 nm or a blue laser having a wavelength of around 400-500 nm. Red pointer lasers, e.g., 656 nm wavelength, are often used, but can be difficult to see in a surgical context.

Examples

Medical laser systems can include a crystal-based laser operably connected to an emission port such that coherent light produced by the crystal-based laser is directed out of the emission port, a power supply operably connected to the crystal-based laser, a controller operably connected to both the crystal-based laser and the power supply, a plurality of heat sinks, a fluid conduit forming a single closed fluid circuit, a fluid substantially filling the fluid conduit, a pump operable to circulate the fluid through the fluid conduit, and a heat exchanger. In such systems at least one heat sink can be in thermal contact with each of the crystal-based laser and the power supply, the fluid can be in thermal contact with each of the heat sinks, the heat exchanger can be in thermal contact with both (a) the fluid and (b) ambient surroundings, and the system can include no other active cooling mechanism.

In some such systems, the crystal-based laser can be, for example, a pulsed laser and/or a YAP laser. In such systems, the pump can be a magnetic drive pump. In some such systems, the crystal-based laser can be adapted to emit light having a wavelength in the range of 1000 to 1500 nanometers, or for example about 1341 nanometers. In some such systems, the crystal-based laser can be adapted to emit with a predetermined power and wavelength into a predetermined solid angle sufficient to cause cutting of tissue when the emission port is positioned at a first predetermined distance from the tissue, and coagulation when the emission port is positioned at a second greater predetermined distance from the tissue. In some such systems the predetermined solid angle has an opening angle of about 17 degrees. In some such systems the fluid is a liquid, for example water.

Medical laser systems can include a crystal-based laser, a power supply operably connected to the crystal-based laser, a controller operably connected to both the crystal-based laser and the power supply, an input operably connected to the controller, and a memory operably connected to the controller. In such systems the controller can be suitably programmed to (a) when the input is activated by a user, activate the crystal-based laser by causing the power supply to supply power to the laser, and (b) record data in the memory, the data being indicative of the activation of the laser. The memory can be a removable memory medium, for example a USB flash drive. In some embodiments, the memory can be connected to the controller locally or through a computer network such as the internet or a local area network, or through a wireless communications protocol such as Bluetooth.

In some such systems, the recorded data can be collated on at least one of, or any combination of (i) a per procedure basis, (ii) a per patient basis, and (iii) a per instrument basis. In some such systems, the recorded data can include at least one of, or any combination of (i) a total dosage of electromagnetic radiation emitted by the crystal-based laser, (ii) a duration of the activation of the crystal-based laser, (iii) a wavelength or wavelengths of light emitted by the crystal-based laser, (iv) an instantaneous and/or time-averaged power of the crystal-based laser, (v) the time that a single element of the system has been in use, (vi) the time that the entire system has been in use, and (vii) the time since or until scheduled system maintenance.

Medical laser systems can include a crystal-based laser, an electrosurgery or electrocautery element, a power supply operably connected to both the crystal-based laser and the electrosurgery or electrocautery element, the power supply being operable in a plurality of modes, each mode supplying a different power level, a controller operably connected to the crystal-based laser, the electrosurgery or electrocautery element, and the power supply, and an input operably connected to the controller. In such systems the controller can be suitably programmed to, when the input receives a first signal, cause the power supply to supply power to the crystal-based laser in a first mode sufficient to cause the laser to cut or coagulate tissue, and when the input receives a second signal, cause the power supply to supply power to the electrosurgery or electrocautery element in a second mode sufficient to cause the electrosurgery or electrocautery element to cut or coagulate tissue. In some such systems, in the second mode the power supply can supply power to the electrosurgery or electrocautery element as a radiofrequency waveform. In some such systems the electrosurgery or electrocautery element is a partially electrically insulated wire loop.

Medical laser systems can include a crystal-based laser configured, when activated, to emit laser light having wavelength in the range of 1000 to 2000 nanometers, a pointer laser configured, when activated, to emit visible green or blue laser light having a wavelength in the range of 400 to 620 nanometers, a power supply operably connected to both the crystal-based laser and the pointer laser, a controller operably connected to the power supply, the crystal-based laser and the pointer laser, and an input operably connected to the controller. In such systems the controller can be suitably programmed to when the input receives a first signal, cause the power supply to supply power to the pointer laser and not to the crystal-based laser, and when the input receives a second signal, cause the power supply to supply power to both the pointer laser and the crystal-based laser. In such systems the crystal-based laser and pointer laser can be configured to be focused on a common target position.

A method of using a laser surgical system can make use of a system that includes a crystal-based laser operably connected to an emission port such that coherent light produced by the laser is directed out of the emission port, a controller operably connected to the crystal-based laser, and a power supply operably connected to the crystal-based laser and the controller. The system can be adapted to, when activated, emit from the emission port coherent light of a predetermined power and predetermined wavelength into a predetermined solid angle. The method can include (1) positioning the emission port at a predetermined cutting distance from a tissue to be cut, (2) cutting the tissue to be cut by activating the system while the emission port is at the predetermined cutting distance from the tissue to be cut, (3) positioning the emission port at a predetermined coagulation distance from a tissue to be coagulated, and (4) coagulating the tissue to be coagulated by activating the system while the emission port is at the predetermined coagulation distance from the tissue to be coagulated.

Various processes of the controller described above may be implemented in software, hardware, firmware, or any combination thereof. The processes are preferably implemented in one or more computer programs executing on the controller. Each computer program can be a set of instructions (program code) in a code module resident in the random access memory of the controller. Until required by the controller, the set of instructions may be stored in another computer memory (e.g., in a hard disk drive, or in a removable memory such as an optical disk, external hard drive, memory card, or flash drive) or stored on another computer system and downloaded via the Internet or other network.

Having thus described several illustrative embodiments, it is to be appreciated that various alterations, modifications, and improvements will readily occur to those skilled in the art. Such alterations, modifications, and improvements are intended to form a part of this disclosure, and are intended to be within the spirit and scope of this disclosure. While some examples presented herein involve specific combinations of functions or structural elements, it should be understood that those functions and elements may be combined in other ways according to the present disclosure to accomplish the same or different objectives. In particular, acts, elements, and features discussed in connection with one embodiment are not intended to be excluded from similar or other roles in other embodiments. Additionally, elements and components described herein may be further divided into additional components or joined together to form fewer components for performing the same functions.

Accordingly, the foregoing description and attached drawings are by way of example only, and are not intended to be limiting.

The invention claimed is:

1. A medical laser system, comprising:
   a crystal-based laser;
   a power supply for powering the crystal-based laser;
   a controller operably connected to the crystal-based laser and the power supply; and
   a liquid cooling system, comprising:
      a conduit circuit through which a cooling liquid can circulate, said conduit circuit thermally coupled to the crystal-based laser such that the cooling liquid in the conduit circuit absorbs heat from the crystal-based laser;
      one or more heat sinks thermally coupled to the conduit circuit and to said power supply such that said cooling liquid in the conduit circuit absorbs heat from the power supply;
      a pump for driving the cooling liquid through the conduit circuit;
      a heat exchanger for cooling the cooling liquid in the conduit circuit; and
      a filter for removing particulates in the cooling liquid, said filter being connected to said conduit circuit in parallel to the crystal-based laser or the one or more heat sinks.

2. The system of claim 1, wherein the medical laser system includes no other active cooling mechanism.

3. The system of claim 1, wherein the pump is a magnetic drive pump.

4. The system of claim 1, wherein the crystal-based laser is a pulsed laser or a YAP laser.

5. The system of claim 1, wherein the crystal-based laser is operable to emit light having a wavelength in the range of 1000 to 1500 nanometers.

6. The system of claim 5, wherein the crystal-based laser is operable to emit light having a wavelength of about 1341 nanometers.

7. The system of claim 1, wherein the cooling liquid is water.

8. The system of claim 7, wherein the water is deionized water or distilled water.

9. The system of claim 1, wherein the liquid cooling system further comprises a tank connected to the conduit circuit for supplying the liquid coolant to the conduit circuit.

10. The system of claim 9, wherein the tank is in an elevated position relative to the crystal-based laser.

11. The system of claim 9, further comprising a cooling liquid sensor in said tank for detecting a surface level of the cooling liquid in the tank.

12. The system of claim 1, further comprising a flow restrictor in the conduit circuit for restricting flow of the cooling liquid through the filter.

13. The system of claim 12, wherein the ratio of flow of the cooling liquid through the filter to flow of the cooling liquid through the crystal-based laser and the one or more heat sinks is about 1:5.

14. A method of cooling a medical laser system comprising a crystal-based laser, a power supply for powering the crystal-based laser, and a controller operably connected to the crystal-based laser and the power supply, the method comprising the steps of:
   circulating a cooling liquid through a conduit circuit thermally coupled to the crystal-based laser and one or more heat sinks thermally coupled to the power supply such that said cooling liquid in the conduit circuit absorbs heat from the crystal-based laser and the power supply;
   cooling the cooling liquid in the conduit circuit; and
   diverting some but not all of the cooling liquid flowing through the conduit circuit to a filter for removing particulates in the cooling liquid, said filter being connected to said conduit circuit in parallel with the crystal-based laser or the one or more heat sinks.

15. The method of claim 14, wherein the ratio of flow of the cooling liquid through the filter to flow of the cooling liquid through the crystal-based laser and the one or more heat sinks is about 1:5.

16. The method of claim 14, further comprising flowing the cooling liquid in the conduit circuit through a replenishment tank.

17. The method of claim 16, further comprising detecting a surface level of the cooling liquid in the tank.

18. The method of claim 16, further comprising maintaining the tank in an elevated position relative to the crystal-based laser.

19. A medical laser system, comprising:
a crystal-based laser;
a power supply for powering the crystal-based laser;
a controller operably connected to the crystal-based laser and the power supply; and
a liquid cooling system, comprising:
- a conduit circuit through which a cooling liquid can circulate, said conduit circuit thermally coupled to the crystal-based laser such that the cooling liquid in the conduit circuit absorbs heat from the crystal-based laser;
- one or more heat sinks thermally coupled to the conduit circuit and to said power supply such that said cooling liquid in the conduit circuit absorbs heat from the power supply;
- a pump for driving the cooling liquid through the conduit circuit;
- a heat exchanger for cooling the cooling liquid in the conduit circuit;
- a replenishment tank connected to the conduit circuit for supplying the liquid coolant to the conduit circuit, wherein the replenishment tank is in an elevated position relative to the crystal-based laser.

20. The system of claim 19, further comprising a filter for removing particulates in the cooling liquid, said filter being connected to said conduit circuit in parallel with the crystal-based laser or the one or more heat sinks.

21. The system of claim 19, further comprising a cooling liquid sensor in said tank for detecting a surface level of cooling liquid in the tank.

22. The system of claim 19, further comprising a flow restrictor in the conduit circuit for restricting flow of the cooling liquid through the filter.

23. The system of claim 22, wherein the ratio of flow of the cooling liquid through the filter to flow of the cooling liquid through the crystal-based laser and the one or more heat sinks is about 1:5.

* * * * *